United States Patent [19]
McKeel

[11] Patent Number: 5,527,265
[45] Date of Patent: Jun. 18, 1996

[54] ORTHOPEDIC AIRFLOW CAST PAD AND METHOD

[76] Inventor: William H. McKeel, 1801 W. Norton, Suite 309, Springfield, Mo. 65803

[21] Appl. No.: 291,181

[22] Filed: Aug. 16, 1994

[51] Int. Cl.$^6$ ........................................................ A61F 5/00
[52] U.S. Cl. ........................ 602/6; 602/3; 602/5; 428/71
[58] Field of Search .................................. 602/5, 6, 8, 14, 602/15, 23, 26, 60, 62, 63; 428/71

[56] References Cited

U.S. PATENT DOCUMENTS

| | | | |
|---|---|---|---|
| 2,958,325 | 11/1960 | Claydon | 602/6 |
| 3,307,537 | 3/1967 | Simon et al. | 602/14 |
| 3,998,220 | 12/1976 | Cleer, Jr. et al. | 128/91 |
| 4,387,710 | 6/1983 | Beatty, III | 128/91 |
| 4,578,456 | 3/1986 | Spann | 602/6 X |
| 4,766,890 | 8/1988 | Hollrah | 128/89 |
| 4,888,225 | 12/1989 | Sandvig et al. | 428/71 |
| 4,928,678 | 5/1990 | Grim | 602/14 X |
| 4,946,726 | 8/1990 | Sandvig et al. | 428/76 |
| 5,277,954 | 1/1994 | Carpenter et al. | 428/71 |
| 5,324,252 | 6/1994 | Libbey et al. | 602/5 |

Primary Examiner—Richard J. Apley
Assistant Examiner—Kim M. Lee
Attorney, Agent, or Firm—Richard J. Grundstrom

[57] ABSTRACT

The orthopedic airflow cast pad of this invention consists basically of a base pad with a plurality of cushions projection outward in a particular pattern to create a plurality of air channels. The orthopedic airflow cast pad can be molded or formed from a single sheet of a water impermeable material, such as a thermal closed cell polyethylene.

The orthopedic airflow cast pad is used to immobilize a fractured limb. The broken limb, in which the bone has been set, is placed across the cushions on the pad. The pad is wrapped around the limb. Excess material is cut and trimmed with a scissors. The pad is circled taped around the pad to hold it in proper position. The outer ends of the orthopedic airflow cast pad are folded over to form folded edges. The pad and folded edges can then be completely wrapped with a water resistant tape to form a complete water resistant cast.

The pad allows air flow to the skin through the air channels to minimize rashes and itching under the cast. The material used is water impervious to allow rinsing under the cast, eliminate odor collection and reduce moisture against the skin. The pad adjusts to swelling and reduction in swelling for a more consistent and comfortable fit of the cast.

9 Claims, 7 Drawing Sheets

ORTHOPEDIC AIRFLOW CAST PAD AND METHOD

BACKGROUND OF THE INVENTION

The present invention relates to an orthopedic airflow cast pad and more particularly to a new casting pad and method of casting a broken limb to make a light weight water resistant cast.

Typically, most broken limbs, such as arms and legs, are immobilized in a cast for the healing process. The cast immobilizes the limb to allow the bone fracture to mend itself in proper position. The cast most often used consists of layers of cloth tape around the limb. The layers of cloth tape are covered with plaster or with a newer fiberglass cast. The plaster cast is typically supplied in the form of a casting tape made with a fiber inner tape having a plaster covering. The plaster is wetted to bond the plaster together to form the cast after the tape is wrapped around and over the layers of cloth tape. Once bonded the plaster binds together to make a solid plaster cast.

The plaster in the casts made in this manner dissolves when wet. Therefore, care must be taken to prevent the cast from getting wet. Additionally, any moisture that gets under the cast wets the cloth tape within the plaster cast. The cloth tape can get wet from washing and from perspiration. The wet cloth tape causes skin irritation and mildews after a short time. The mildew creates an unpleasant odor. Since the plaster cast cannot be wetted, washing and cleaning is very difficult and skin irritants and dirt cannot be washed out.

The plaster cast is also heavy and rigid and it does not allow for swelling and reduction in the limb. The plaster cast most often cannot be made until the swelling in the limb has gone down. If placed before the swelling is reduced, the cast will become too loose and become ineffective in immobilizing the limb. If the cast is place too early and the limb is still swelling, the cast will be come too tight and create pressure. When swelling occurs or continues after the cast has been placed, the cast often has to be split to relieve pressure.

The fiberglass cast which is also in use today has some advantages over the plaster cast, but has several problem of the same problems encountered with the plaster cast. The fiberglass cast itself is lighter, water resistant and more durable than the plaster cast. However, the cloth covering against the skin may become wet just as in the plaster cast. If this happens, the cast has to be removed to eliminate odors, mildew, and skin irritation just as in the plaster cast. There is no means to dry the cloth under the cast if it becomes wet. The fiberglass cast is also rigid like the plaster cast. It does not adjust for swelling and reduction to provide a better and more comfortable fit.

Accordingly, it is an object of the present invention to provide an orthopedic airflow cast pad adapted to overcome the disadvantages of the plaster and fiberglass cast that are typically used today. With the orthopedic airflow cast pad of this invention it has been found that the cast will fit better, help to reduce slippage and adjust to normal swelling and shrinkage of the callus around the fractured bone.

Another object of the present invention is to provide an improved orthopedic airflow cast pad constructed to provide a light weight cast for immobilizing a fractured limb that is water resistant. Since the orthopedic airflow cast pad of this invention is water resistant, irritants and other matter can be flushed out without affecting the cast or the fit. This helps to eliminate itching and odors associated with typical plaster casts.

A further object of the present invention is to provide an orthopedic airflow cast pad that promotes airflow between the skin and the cast. The orthopedic airflow cast pad of this invention contains multiple air channels to allow airflow to the skin. These air channels provides a means of irrigating and washing the skin under the cast and to provide a means of allowing water and moisture to runoff.

Still another object of the present invention is to provide an orthopedic airflow cast pad adapted for easy application by a physician and to maintain cost to a minimum for the patient. The orthopedic airflow cast pad of this invention is easily applied by following simple instructions.

SUMMARY OF THE INVENTION

To accomplish the foregoing and other objects of this invention there is provided an orthopedic airflow cast pad and more particularly a cast pad that is light weight, water resistant which is easily applied to immobilize a fractured limb.

The orthopedic airflow cast pad of this invention includes a base pad made from a water impervious material. The base pad typically has a top surface and a bottom surface. A plurality of cushions projects outward from the top surface of the base pad. The cushions are arranged in a pattern to form a plurality of air channels. The air channels allow airflow length wise and cross wise across the top surface of the base pad and over the skin. The pad can be made in various sizes based on the particular application. The cushion can may vary in size and firmness to accommodate the needs of the patients from infants to large adults. In addition, the pad can be cut to fit the patient using a pair of scissors.

The pad allows air flow to the skin to reduce rashes and itching under the cast. The material used is water impervious to allow rinsing under the cast, eliminate odor collection and reduce moisture against the skin. The pad also adjusts to swelling and reduction in swelling for a more consistent fit of the cast.

These and other objects and features of the present invention will be better understood and appreciated from the following detailed description of the main embodiment thereof, selected for purposes of illustration and shown in the accompanying drawings.

DETAILED DESCRIPTION

Referring now to the drawings, FIGS. 1–5, there is shown the preferred embodiment of the orthopedic airflow cast pad 10 of this invention.

The orthopedic airflow cast pad 10 of this invention consists basically of a base pad 12, a plurality of cushions 14 and a plurality of air channels 16 formed between the cushions 14. The base pad 12 and cushions 14, in the best mode contemplated, are molded from a single sheet of water impermeable closed cell thermal foam polyethylene.

This material, closed cell thermal foam polyethylene, has been found to provide adequate compression and expansion to allow for swelling and reduction of the limb for a better fit and to reduce slippage. It is also water impermeable to allow washing and flushing of irritants. The air channels 16 allows air flow between the cast pad 12 and patient's skin as well as allowing water and moisture to runoff. The ability to wash and flush under the cast minimizes rashes and itching and helps to eliminate odors.

When used with fiberglass or plastic cast wrap there is less weight and more comfort than the conventional plaster cast. Since these wraps are also water resistant, the patient can wash, bath and take showers without much regard to the cast. The cast can be dripped dried by placing the cast at a slight angle or air can be blown into the air channels 16. The pattern of the air channels 16 will provide airflow to the majority of the skin surface under the cast. The airflow will pickup and remove moisture from under the cast. These are vast improvements over the conventional plaster cast and it is also the first major change in orthopedic cast padding.

The preferred embodiment and the best mode contemplated of the orthopedic airflow cast pad of the present invention are herein described. However, it should be understood that the best mode for carrying out the invention hereinafter described is offered by way of illustration and not by the way of limitation. It is intended that the scope of the invention include all modifications that incorporate its principal design features.

The base pad 12 and cushions 14 are, in the preferred embodiment formed from a single sheet of a water impermeable material. The orthopedic airflow cast pad 10, in the best mode contemplated, are available in two sizes, 12 inches by 12 inches and 24 inches by 30 inches. The smaller size would typically be used on an arm or perhaps a leg of a child and the larger size would be used on a leg of an adult. The orthopedic airflow cast pad 10 can also be made in various other sizes depending on the application and need. The pad once placed can be cut with scissors for a perfect fit on the patient.

A plurality of cushions 14 project outward from the top surface of the base pad in a specific pattern, in the preferred embodiment. The cushions, in the best mode contemplated are formed by molding along with the base pad 12. The cushions 14 can be made in varying size and firmness to accommodate infants to large adults. In the preferred embodiment and best mode contemplated, the pattern of cushions 14 are arranged in a series of cushions in a plurality of parallel rows. Each cushion, in the best mode contemplated are one and a quarter (1¼) inch long, one quarter (¼) inch wide and projecting outward from the base bad 12 one quarter (¼) inch. The cushions 14 in each row are separated by spaces. Each space between the cushions 14 are one quarter (¼) of an inch. The cushions and spaces between the cushions are staggered in alternating rows. This pattern staggers the spaces from row to row.

The pattern of cushions 14 creates a plurality of air channels 16. The air channels 16 in this pattern allows airflow both length wise and cross wise across the top surface 18 of the base pad 12. Length wise the air channels 16 are straight between and parallel with the rows. Cross wise the air channels 16 are staggered through the staggered spaces between cushions in the rows. The spaces are staggered to maximize air flow to the skin. The staggered spaces will prevent air from just flowing straight through.

The orthopedic airflow cast pad 10 is used to immobilize a fractured limb such as an arm 22 or leg. It is intended to be used in place of the traditional plaster cast or newer fiberglass cast. Referring now to FIGS. 6–13, an arm 22 is used to illustrate how the orthopedic airflow cast pad 10 is used. In use, the broken limb 22, in which the bone has been set, is placed across the cushions 14 on the pad 12 with the fracture centered on the pad 12 if possible. In some instances, the bottom surface 20 could also be placed against the skin. This would provide a water resistant cast with additional support. This arrangement would still provide all the benefits discussed herein except the airflow to the skin. Since the bottom surface 20 is mainly flat the airflow would be more restricted.

It is also possible, in another embodiment not shown, to have cushions 14 projecting outward from the bottom surface 20 as well as the top surface 18. This embodiment results in a reversible orthopedic airflow cast pad that can be used with equal results either way.

Figure 1:
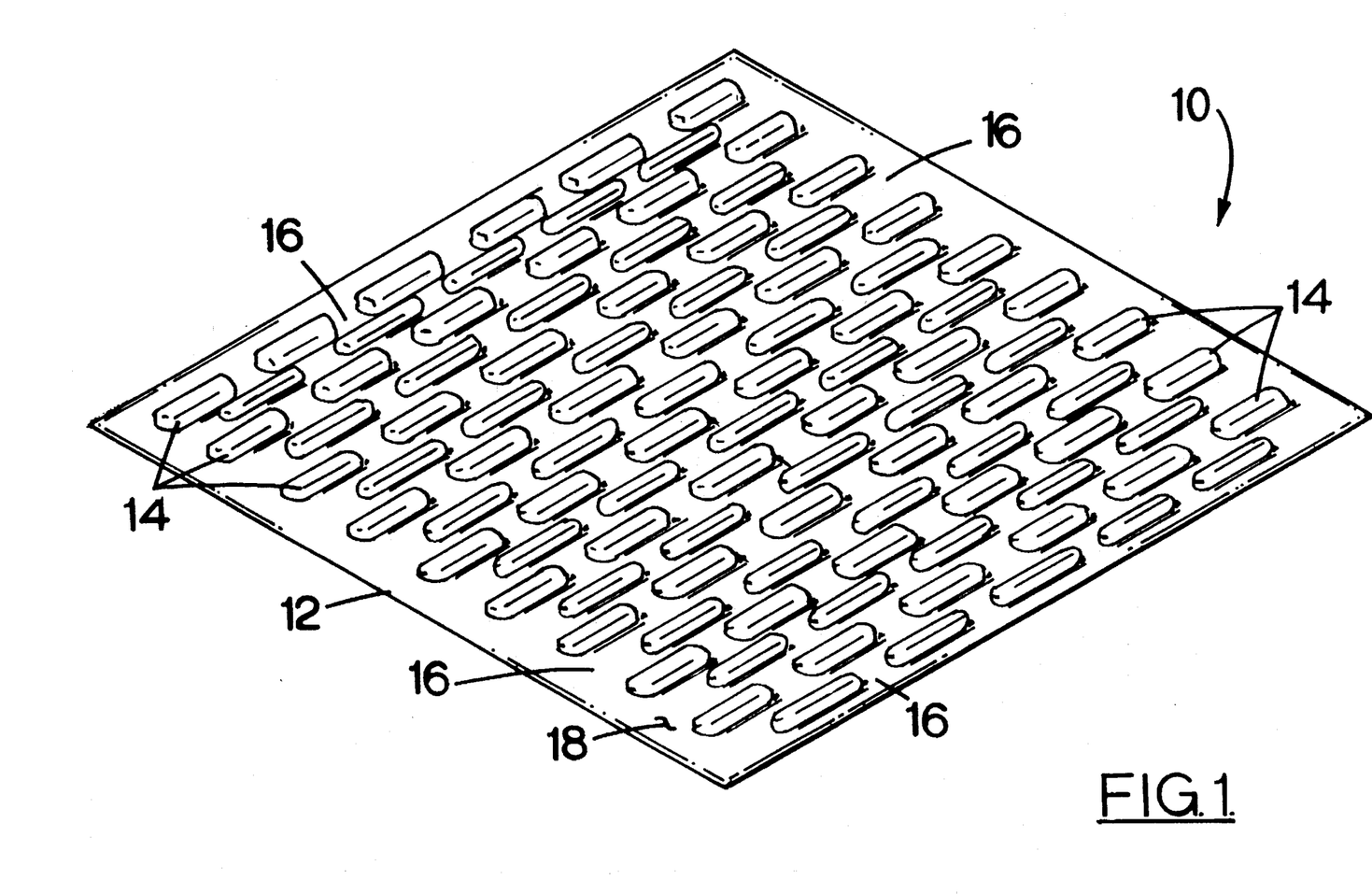
FIG. 1 is an isometric view of the top surface of the orthopedic airflow cast pad of this invention.
Figure 2:
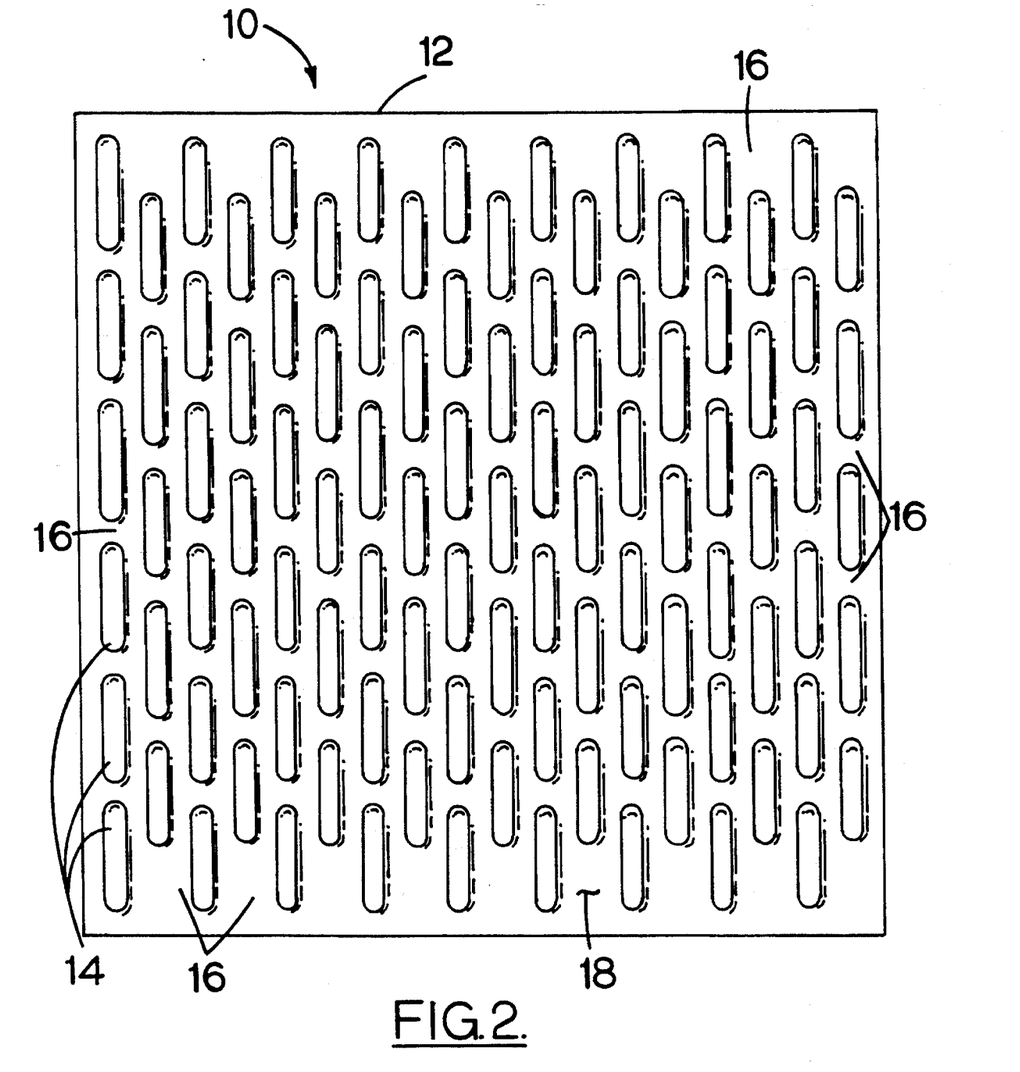
FIG. 2 is a top view of the preferred embodiment of the orthopedic airflow cast pad.
Figure 3:
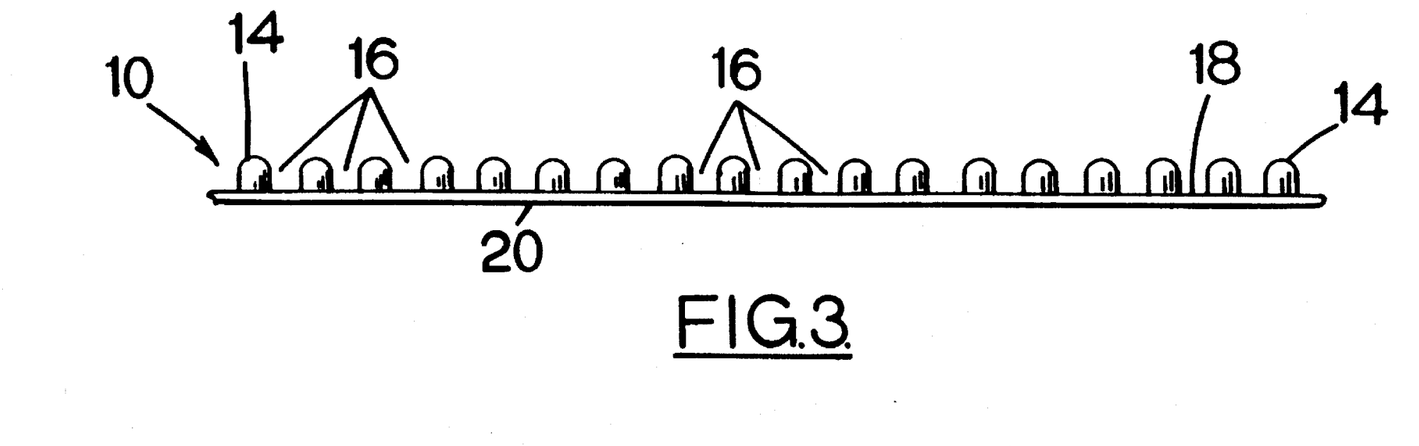
FIG. 3 is an end view of the orthopedic airflow cast pad.
Figure 4:
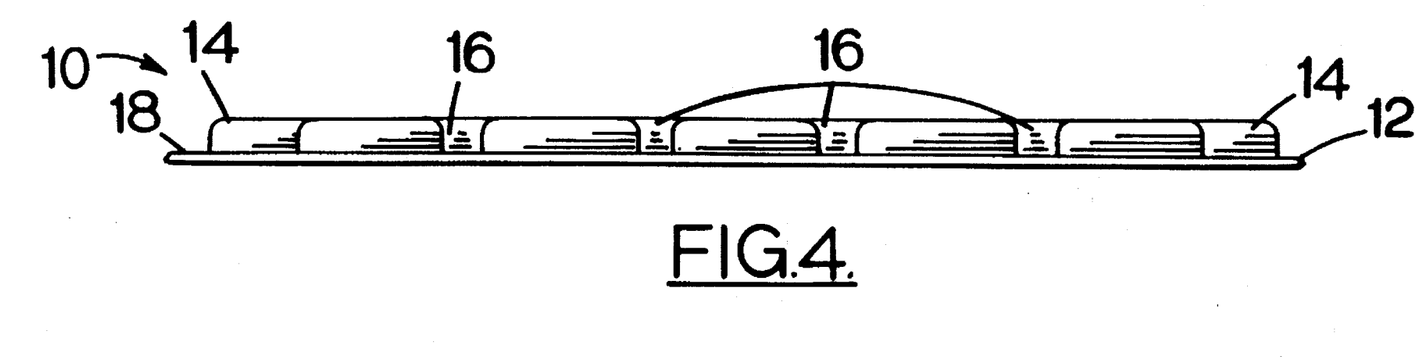
FIG. 4 is a side view of the orthopedic airflow cast pad.
Figure 5:
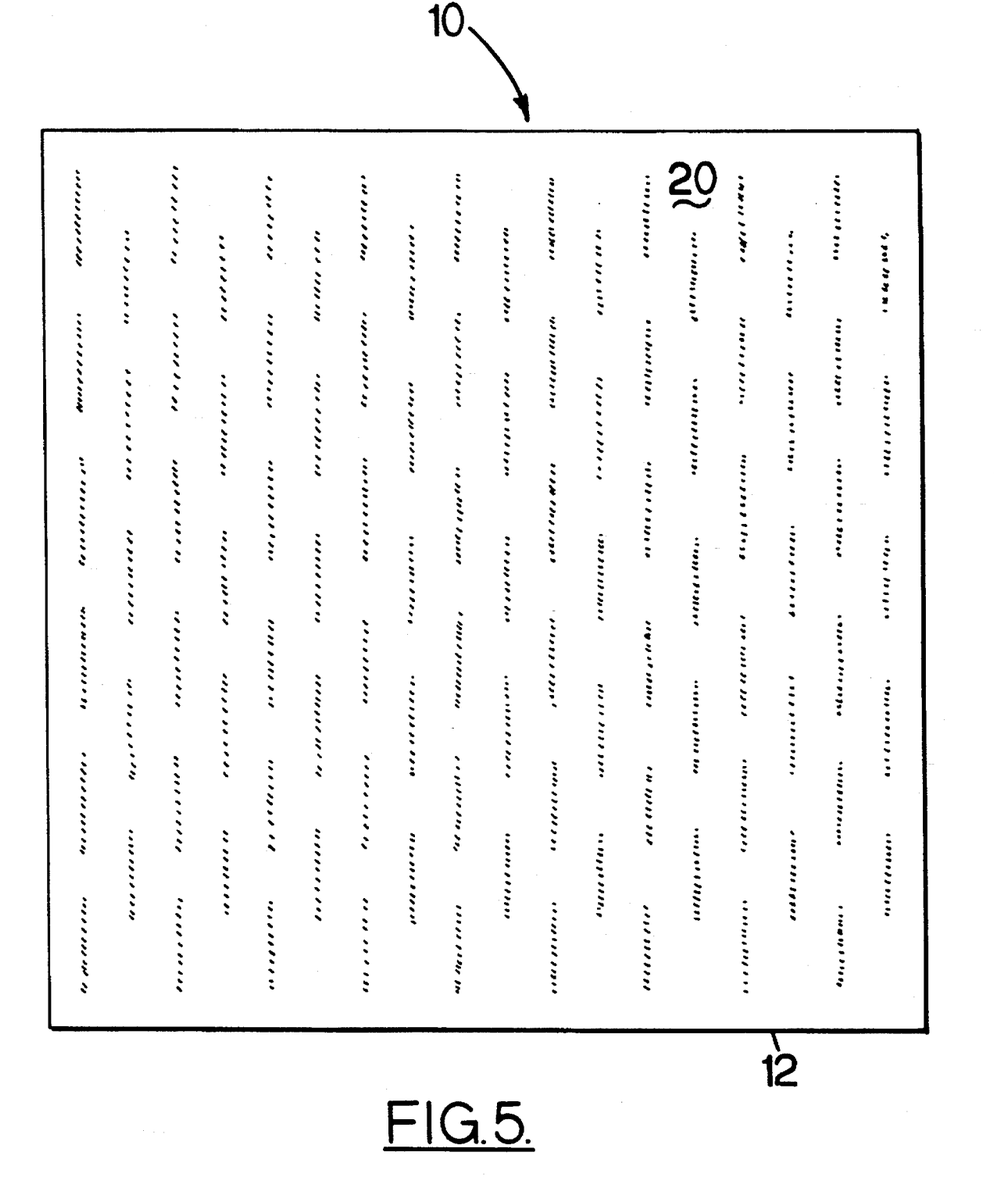
FIG. 5 is a bottom view of the orthopedic airflow cast pad.
Figure 6:
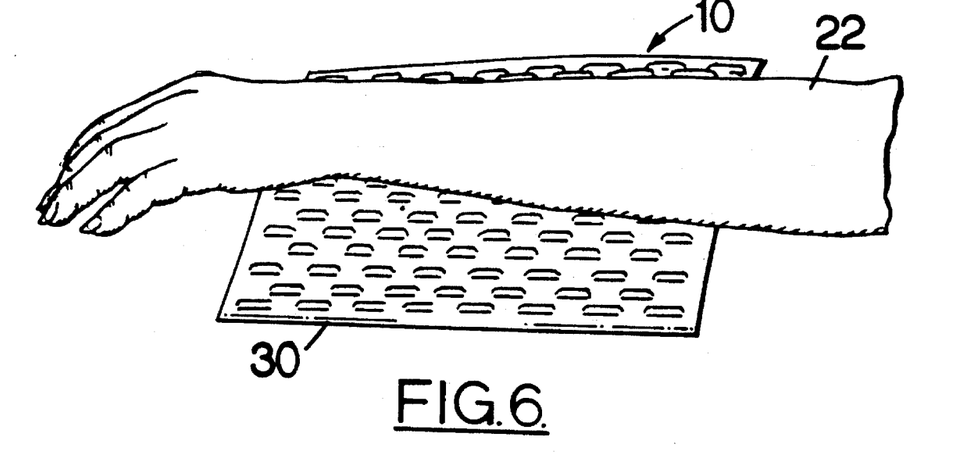
FIG. 6 shows the initial step of laying a limb (ie an arm) to be casted on the orthopedic airflow cast pad.
Figure 7:
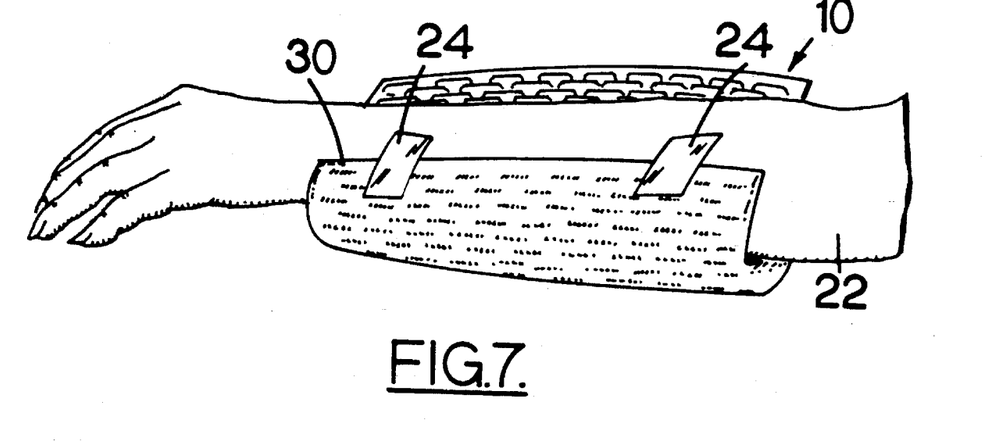
FIG. 7 shows the airflow cast pad being wrapped around a limb (an arm as illustrated) to be casted.
Figure 8:
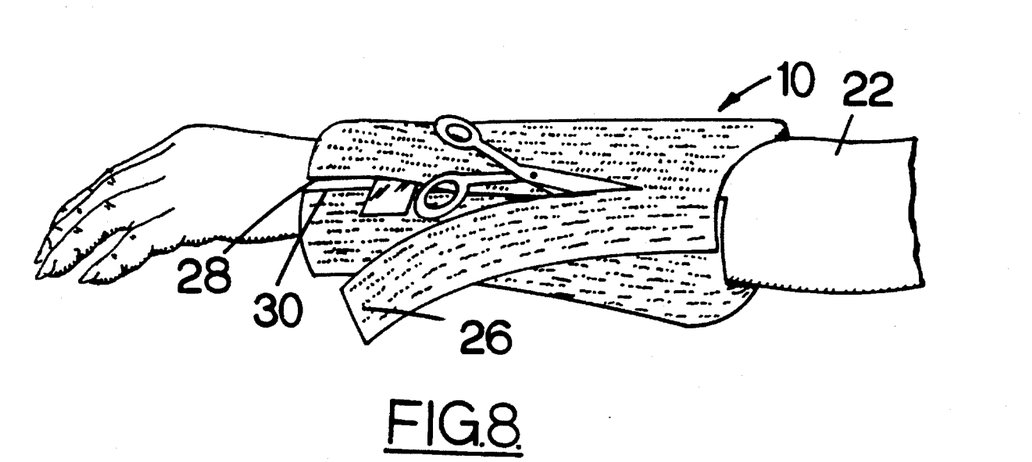
FIG. 8 shows the orthopedic airflow cast pad being cut to fit a particular application.
Figure 9:
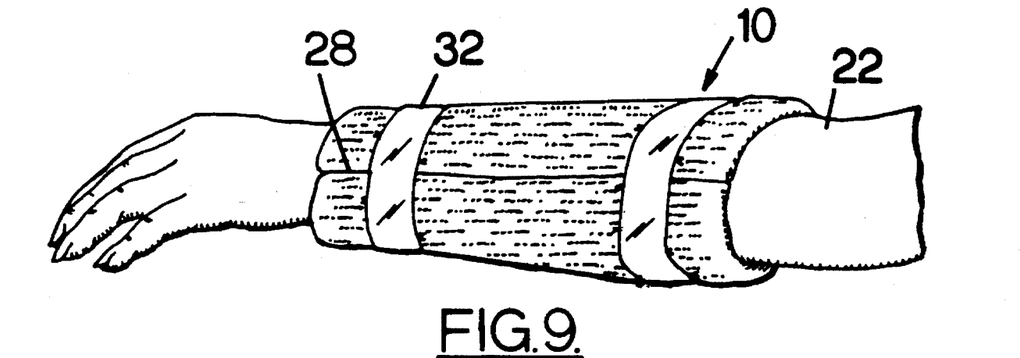
FIG. 9 shows the orthopedic airflow cast pad being held in place with an adhesive tap.
Figure 10:
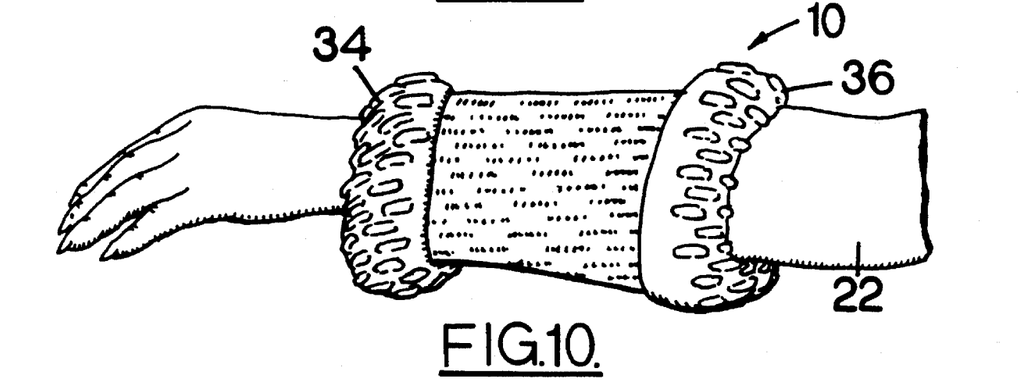
FIG. 10 shows the ends of the orthopedic airflow cast pad being folded over.

After the limb 22 is positioned on the orthopedic airflow cast pad 10, the orthopedic airflow cast pad 10 is wrapped around the fractured limb 22. One edge 30 of the orthopedic airflow cast pad may be temporarily taped 24 to the limb 22, as shown in FIG. 7, as the other end is brought around the limb 22. Excess material 26 is cut and trimmed with a scissors, as shown in FIG. 8. The orthopedic airflow cast pad should fit snugly around the limb 22 with the cut edge 28 butting up against the uncut edge 30. The temporary tape 24 should be removed, if used. The orthopedic airflow cast pad 10 is then circled taped 32 around to hold it in proper position. The outer ends of the orthopedic airflow cast pad are folded over to form folded edges 34 and 36. Ideally, the circle tape 32 is positioned approximately one and a half (1½) inches from the end of the orthopedic airflow cast pad. Then the ends are folded and rolled over to cover the circle tape 32. FIG. 10.

Figure 11:
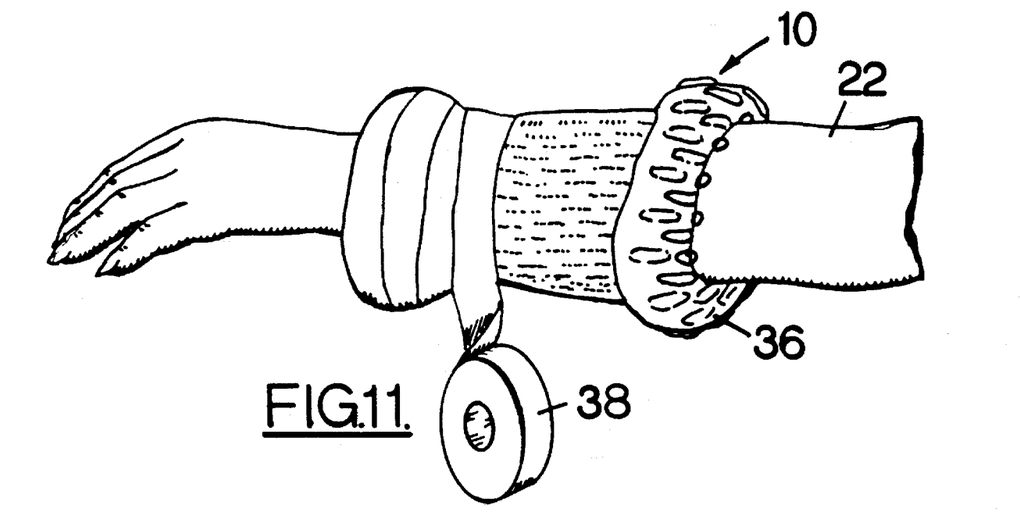
FIG. 11 shows the orthopedic airflow cast pad in place on an arm being wrapped with tape.
Figure 12:
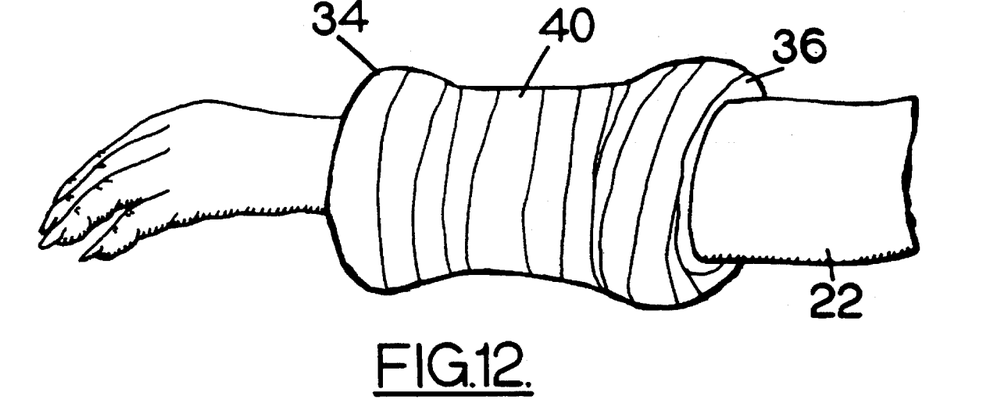
FIG. 12 shows the orthopedic airflow cast pad being completely wrapped in tape.

The orthopedic airflow cast pad 10 and folded edges 34 and 36 is wrapped with fiberglass tape, plastic cast wrap or other water-resistant tape 38 to form a complete water resistant cast 40. Approximately one half (½) inch of the folded ends 34 and 36 are left exposed to prevent the air channels 16 from being blocked.

Figure 13:
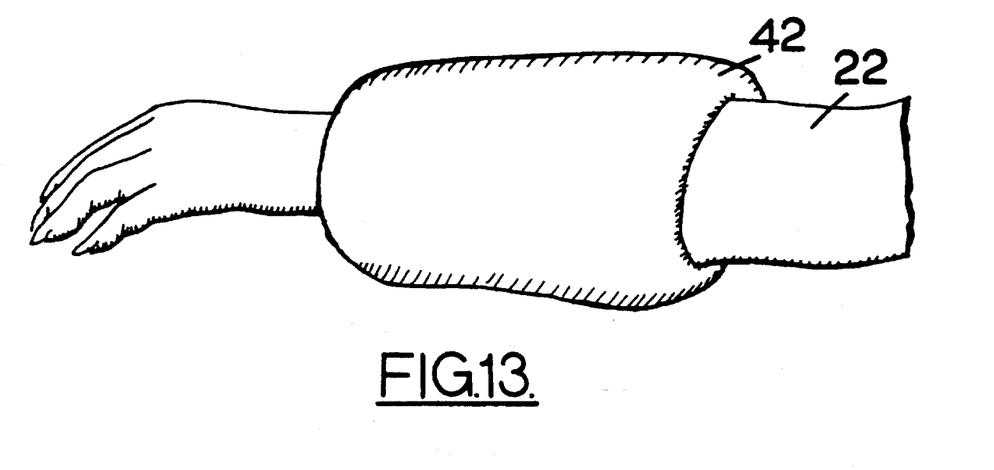
FIG. 13 shows the orthopedic airflow cast pad being covered with additional or optional casting.

As illustrated in FIG. 13, the completed cast 40 may be covered with a plaster covering 42 to provide a more rigid cast. This would only be necessary in extreme cases where the additional rigidness is needed. It is not anticipated that plaster would be used or needed very often.

Having described the invention in detail, those skilled in the art will appreciate that modifications may be made of the invention without departing from the spirit of the inventive concept herein described.

Therefore, it is not intended that the scope of the invention be limited to the specific and preferred embodiments illustrated and described. Rather, it is intended that the scope of the invention be determined by the appended claims and their equivalents.

What is claimed is:

1. An orthopedic airflow cast pad, used in place of cloth wrapping placed between the skin and cast material in typical orthopedic cast applications comprising:

a base pad made from a single sheet of water impermeable material having a top surface and a bottom surface, said base pad being wrapable around a limb of an individual and covered with a cast material;

a plurality of cushions in a specific pattern projecting outward from said top surface of said base pad, said cushions being of the same material as said base pad and having adequate compression and expansion characteristics to allow for swelling and reduction of the limb, said cushions being positioned against the skin of the limb; and a plurality of air channels formed between said cushions to allow airflow length wise and cross wise between and across the skin on the limb and said top surface of said base pad, and said air channels allowing water and moisture to run off for rinsing and cleansing the skin under the cast and to maximize air flow across the skin to dry the skin.

2. The orthopedic airflow cast pad as set forth in claim 1 in which said cushions comprise a plurality of parallel rows of uniform inline cushions, said cushions in said parallel rows of uniform inline cushions being separated by a space and said space between said cushions being staggered from row to row with said cushions making said air channels straight between and parallel with said parallel rows of uniform inline cushions and staggered across said parallel rows of uniform inline cushions through said staggered spaces between said cushions.

3. The orthopedic airflow cast pad as set forth in claim 1 in which said base pad and said cushions are molded as a single sheet from a thermal foam closed cell polyethylene.

4. The orthopedic airflow cast pad as set forth in claim 1 further comprising a plurality of cushions extending outward from said bottom surface of said base pad, said cushions forming air channels length wise and cross wise on said bottom surface.

5. An orthopedic airflow cast pad, used in place of cloth wrapping placed between the skin and cast material in typical orthopedic cast applications comprising:

a base pad formed from a single sheet of a water impermeable material having a top surface and a bottom surface, said base pad being placed between a casting material and the skin of a limb on which a cast is being applied;

a plurality of cushions projecting outward from said top surface of said base pad, said cushions being of the same material as said base pad, said cushions comprising a series of cushions in a plurality of parallel rows, said cushions in said parallel rows being separated by spaces and said spaces between said cushions being staggered from row to row, said cushions being placed against the skin on the limb on which a cast is being applied; and a plurality of air channels formed between said cushions to allow airflow length wise and cross wise between and across the skin of the limb and said top surface of said base pad, said cushions arranged to make said air channels straight length wise between and parallel with said parallel rows and staggered cross wise across said parallel rows through said staggered spaces between said cushions, to maximize air flow across the skin to dry the skin and to allow water and moisture to run off for rinsing and cleansing the skin under the cast.

6. The orthopedic airflow cast pad as set forth in claim 5 in which said base pad and cushions are molded from a closed cell cross linked polyethylene.

7. A method of making and using an orthopedic airflow cast pad having a top portion and a bottom portion, used in place of cloth wrapping in an orthopedic cast application, to make a water resistant cast for a broken limb, in which steps comprise:

constructing a base pad, from a single sheet of water impermeable material having a top surface, a bottom surface, top edge, bottom edge and two side edges which form inside edges when said orthopedic airflow cast pad is in use, with a pattern of cushions projecting outward from said base pad, said pattern of cushions forming a plurality of air channels between said cushions, which maximizes airflow across the skin;

placing a broken limb, in which the bone has been set, across said cushions on said orthopedic airflow cast pad;

wrapping said orthopedic airflow cast pad around the limb with said cushions contacting skin on the limb, such that said side edges overlap forming said inside edges in a parallel relationship with the limb;

cutting off and trimming excess material from said inside edges of said orthopedic airflow cast pad wrapped around the limb so said inside edges of said orthopedic cast pad butt against each other and said orthopedic airflow cast pad fits snugly against the skin;

taping said orthopedic airflow cast pad around the limb to hold said orthopedic airflow cast pad in position;

folding said top edge and said bottom edge of said orthopedic airflow cast pad over to form folded edges at the top portion and bottom portion of said orthopedic airflow cast pad wrapped around the limb; and wrapping a water resistant tape, to provide rigid support for the limb, around said orthopedic airflow cast pad and said folded edges to form a complete cast made with said orthopedic airflow cast pad and water resistant tape thereby forming a cast that allows water and moisture to run off for rinsing and cleansing the skin under said cast and allowing maximum air flow across the skin to dry the skin.

8. The method of making and using the orthopedic airflow cast pad as set forth in claim 7 in which said step of construction said base pad with a pattern of cushions projection outward from a water impermeable material comprises molding as a single sheet said base pad and cushions from a closed cell polyethylene.

9. The method of making and using the orthopedic airflow cast pad as set forth in claim 7 in which said pattern of cushions in said step of constructing said base pad comprises a series of cushions projecting outward from said base pad in a plurality of parallel rows, separating said cushions in said rows by a spaces, and staggering said spaces between said cushions from row to row, forming said air channels straight between and parallel with said rows and staggered across said rows through said staggered spaces between said cushions.

* * * * *